(12) United States Patent
Maris et al.

(10) Patent No.: US 11,033,228 B2
(45) Date of Patent: Jun. 15, 2021

(54) WEARABLE FATIGUE ALERT DEVICES FOR MONITORING THE FATIGUE STATUS OF VEHICLE OPERATORS

(71) Applicant: Centenary University, Hackettstown, NJ (US)

(72) Inventors: Kyle Maris, Stewartsville, NJ (US); Jeff Rottingen, Ramsey, NJ (US); Matilda Poisseroux, Hackettstown, NJ (US); Colin Hudson, Hackettstown, NJ (US); Eddie Medina, Newton, NJ (US)

(73) Assignee: Centenary University, Hackettstown, NJ (US)

( * ) Notice: Subject to any disclaimer, the term of this patent is extended or adjusted under 35 U.S.C. 154(b) by 0 days.

(21) Appl. No.: 16/593,553

(22) Filed: Oct. 4, 2019

(65) Prior Publication Data

US 2020/0107768 A1 Apr. 9, 2020

Related U.S. Application Data

(60) Provisional application No. 62/742,138, filed on Oct. 5, 2018.

(51) Int. Cl.
*A61B 5/18* (2006.01)
*A61B 5/00* (2006.01)
(Continued)

(52) U.S. Cl.
CPC ............... *A61B 5/681* (2013.01); *A61B 5/18* (2013.01); *A61B 5/6802* (2013.01); *A61B 5/74* (2013.01);
(Continued)

(58) Field of Classification Search
CPC ........... A61B 5/00; A61B 5/0059; A61B 5/01; A61B 5/02; A61B 5/024; A61B 5/04; A61B 5/04001; A61B 5/04004; A61B 5/04005; A61B 5/0408; A61B 5/044; A61B 5/0476; A61B 5/0482; A61B 5/18; A61B 5/681; A61B 5/74; A61B 5/7405; A61B 5/742; A61B 5/7455; A61B 5/746
See application file for complete search history.

(56) References Cited

U.S. PATENT DOCUMENTS

| 9,766,959 B2 * | 9/2017 | Faaborg | A61B 5/0484 |
| 2016/0071393 A1 * | 3/2016 | Kaplan | A61B 5/74 340/539.12 |

(Continued)

*Primary Examiner* — Van T Trieu
(74) *Attorney, Agent, or Firm* — Doherty IP Law Group LLC

(57) ABSTRACT

A wearable fatigue alert device includes a housing that is secured to a wristband. The device includes one or more sensors that are located on the wristband. When the device is worn over a wrist, the one or more sensors are configured to obtain biofeedback data from a wearer for determining the fatigue status of the wearer. The device includes a circuit board having a microprocessor that is in communication with the one or more sensors. The one or more sensors collect and communicate the biofeedback data of the wearer to the microprocessor, which generates an alert signal (e.g., vibration, sound, light) that notifies the wearer that they are becoming fatigued. The microprocessor uses Electrodermal Activity (EDA) technology for evaluating the fatigue status of the wearer.

20 Claims, 2 Drawing Sheets

(51) Int. Cl.
*G06F 3/01* (2006.01)
*G06F 1/16* (2006.01)

(52) U.S. Cl.
CPC .............. *G06F 1/163* (2013.01); *G06F 3/013* (2013.01); *G06F 3/015* (2013.01)

(56) References Cited

U.S. PATENT DOCUMENTS

| | | | |
|---|---|---|---|
| 2016/0367157 A1* | 12/2016 | Blake | A61B 5/0428 |
| 2017/0196497 A1* | 7/2017 | Ray | G16H 40/63 |
| 2017/0215745 A1* | 8/2017 | Felix | A61B 5/0255 |
| 2020/0075039 A1* | 3/2020 | Eleftheriou | G06K 9/00892 |

* cited by examiner

WEARABLE FATIGUE ALERT DEVICES FOR MONITORING THE FATIGUE STATUS OF VEHICLE OPERATORS

CROSS-REFERENCE TO RELATED APPLICATIONS

The present patent application claims benefit of U.S. Provisional Application Ser. No. 62/742,138, filed Oct. 5, 2018, the disclosure of which is hereby incorporated by reference herein.

BACKGROUND OF THE INVENTION

Field of the Invention

The present patent application is generally related to wearable devices such as smart watches, and is more particularly related to wearable devices that alert individuals when they are becoming fatigued or drowsy.

Description of the Related Art

Every day, millions of drivers use personal automobiles to commute back and forth to school, work, and church. Automobile travel occurs over all types of road conditions (e.g., highway, local roads), at all times of the day and night, and in different weather conditions (e.g., snow, rain, dusk).

In addition to personal automobile travel, roads are often filled with commercial trucks that travel back and forth between factories, shipping centers, retails establishments and businesses. Commercial truckers are often required to travel extremely long distances over varying terrain and weather conditions.

Ideally, an individual needs between seven and eight hours of sleep each night. Individuals who often sleep less than the necessary time will build up sleep debt, or sleep deficit. Fatigue, drowsiness, and sleepiness often afflict drivers of personal automobiles and commercial vehicles. Drivers with sleep debt often risk nodding off, and exhibit slower reaction times and impaired decision making when behind the wheel, thereby increasing the risk of involving themselves or others in an accident. Every year, there are tens of thousands of accidents and deaths that occur when drivers fall asleep at the wheel.

Thus, there is a need for a device that alerts a driver when he or she becomes sleepy or drowsy so as to avoid unnecessary accidents and deaths.

SUMMARY OF THE INVENTION

The present patent application is directed to a wearable device that uses biofeedback data to monitor the fatigue status of a wearer, and that alerts the wearer when the biofeedback data indicates that the wearer is becoming fatigued, sleepy, and/or drowsy.

In one embodiment, a wearable fatigue alert device may include a wristband device that is similar in size and configuration to a smart watch. In one embodiment, the device may include a housing that has outer dimensions of about 1.5×1.0 inches.

In one embodiment, the device may be housed upon a wristband such as a silicone wristband. In one embodiment, the device may have one or more sensors that collect biofeedback data from the wearer. In one embodiment, the device may include two sensors built into one or both sides of the wristband.

In one embodiment, the device may include a circuit board having one or more microprocessors, and one or more software applications for evaluating the biofeedback data collected by the one or more sensors for making a determination if a wearer is becoming fatigued.

In one embodiment, the wearable fatigue alert device preferably uses Electrodermal Activity (EDA) technology to detect changes in skin conductance based on sweat gland secretion, which will enable the device to detect when the person wearing the device becomes fatigued (i.e., drowsy). As noted above, the device may use one or more sensors to collect the biofeedback data, which is processed by one or more microprocessors to monitor and evaluate the fatigue status of a wearer.

Electrodermal activity (EDA) is the property of the human body that causes continuous variation in the electrical characteristics of the skin. Historically, EDA has also been known as skin conductance, galvanic skin response (GSR), electrodermal response (EDR), psychogalvanic reflex (PGR), skin conductance response (SCR), sympathetic skin response (SSR) and skin conductance level (SCL). The long history of research into the active and passive electrical properties of the skin by a variety of disciplines has resulted in an excess of names, now standardized to electrodermal activity (EDA). See https://en.wikipedia.org/wiki/Electrodermal_activity.

The traditional theory of EDA holds that skin resistance varies with the state of sweat glands in the skin. Sweating is controlled by the sympathetic nervous system, and skin conductance is an indication of psychological or physiological arousal. If the sympathetic branch of the autonomic nervous system is highly aroused, then sweat gland activity also increases, which in turn increases skin conductance. In this way, skin conductance can be a measure of emotional and sympathetic responses. More recent research and additional phenomena (resistance, potential, impedance, and admittance, sometimes responsive and sometimes apparently spontaneous) suggest that EDA is more complex than it seems, and research continues into the source and significance of EDA. Id.

The study of EDA has led to such important and vital tools as the electrocardiograph (ECG or EKG) and the electroencephalograph (EEG). Id.

In one embodiment, the wearable fatigue alert device will desirably alert the wearer of oncoming fatigue through various alert methodologies or alert signals including vibration signals, sound or audible signals and/or by activating one or more lights disposed on the wearable device. The alert signals may be generated by the one or more microprocessors.

In one embodiment, the wearable fatigue alert device may be equipped with a light emitting diode (LED) that indicates that the device has been turned ON.

In one embodiment, the wearable fatigue alert device may include one or more input elements (e.g., a depressible button), which enables a wearer to set intervals of vibration, to help stay alert, regardless of their fatigue status.

The wearable fatigue alert device disclosed herein may be used by anyone who suffers from sleep deprivation, drowsy driving, and/or narcolepsy. In one embodiment, the device may be used by commercial drivers (e.g., truck drivers). As noted above, truck drivers are behind the wheels of company vehicles for hours at a time. A truck driver may certainly suffer from drowsy driving or sleep deprivation while working long hours at a time.

The wearable fatigue alert device disclosed herein may also be used by taxi drivers, ride share drivers, Uber and Lyft drivers, train conductors, bus drivers, commercial airline pilots and students.

In one embodiment, the wearable device provides an instant alert signal when fatigue is detected. The device will preferably keep drivers alert and focused, which will prevent accidents and save lives.

The wearer device has been designed to reduce the motor vehicle collision rate due to driver fatigue. Statistics indicate that driver fatigue, often referred to as drowsy driving, is responsible for about 20 percent of motor vehicle accidents each year. The wearable fatigue alert device disclosed herein is designed to ensure drivers' safety.

In one embodiment, the wearable device may incorporate an optical heart sensor, an electrical heart sensor, and/or waterproof technology.

In one embodiment, a wearable fatigue alert device may include an optical sensor that tracks eye movement for gathering information about the fatigue status of an individual. In one embodiment, the optical sensor may operate within the infrared range of the light spectrum.

In one embodiment, a system for monitoring the fatigue status of vehicle operators preferably includes one or more central processing units containing one or more databases and one or more software programs adapted to monitor the fatigue status of vehicle operators, and a plurality of wearable fatigue alert devices in wireless communication with the central processing unit. In one embodiment, each wearable fatigue alert device preferably includes a housing, a wristband, whereby the housing is secured to the wristband, and at least one sensor located on the wristband. In one embodiment, the at least one sensor is configured to obtain biofeedback data from a wearer for determining the fatigue status of an individual.

In one embodiment, the one or more software programs may include a wireless, web-based protocol for enabling the wearable fatigue alert devices to be linked with electronic components selected from the group consisting of portable devices, smart phones, tablets, desk top computers, lap top computers, and Cloud computing networks.

In one embodiment, the one or more software programs desirably include an initial set-up protocol that enables users to wear one of the wearable fatigue alert devices for a period of time to establish a baseline for determining when a user is alert and when a user is fatigued.

In one embodiment, the one or more central processing units may include artificial intelligence (AI) for collecting information about users and developing user profiles for each user.

In one embodiment, each of the wearable fatigue alert devices preferably includes a circuit board disposed within the housing, whereby the circuit board includes at least one microprocessor that is in communication with the at least one sensor located on the wristband, and whereby the at least one sensor is configured to collect and communicate the biofeedback data to the at least one microprocessor.

In one embodiment, the at least one microprocessor may include code for generating an alert signal for notifying the wearer that they are becoming fatigued. In one embodiment, the at least one microprocessor may be in wireless communication with the one or more central processing units of the fatigue status monitoring system.

In one embodiment, the system may generate alert signals such as vibration signals, audible signals, and light signals.

In one embodiment, the one or more software programs of the system may include code that utilizes Electrodermal Activity (EDA) technology for evaluating the fatigue status of wearers of a wearable fatigue status device.

In one embodiment, each wearable fatigue alert device may include an optical sensor that tracks eye movements for gathering information about users' alert and fatigue states.

In one embodiment, the device may be worn by long haul truckers.

In one embodiment, the wearable device is designed to detect fatigue in an individual wearing the device.

In one embodiment, the wearable device alerts a wearer when fatigue is detected.

In one embodiment, the wearable device uses Electrodermal Activity (EDA) technology.

In one embodiment, the wearable device detects health levels such as blood pressure and heart rate.

These and other preferred embodiments of the present patent application will be described in more detail below.

DETAILED DESCRIPTION OF PREFERRED EMBODIMENTS

Figure 1:
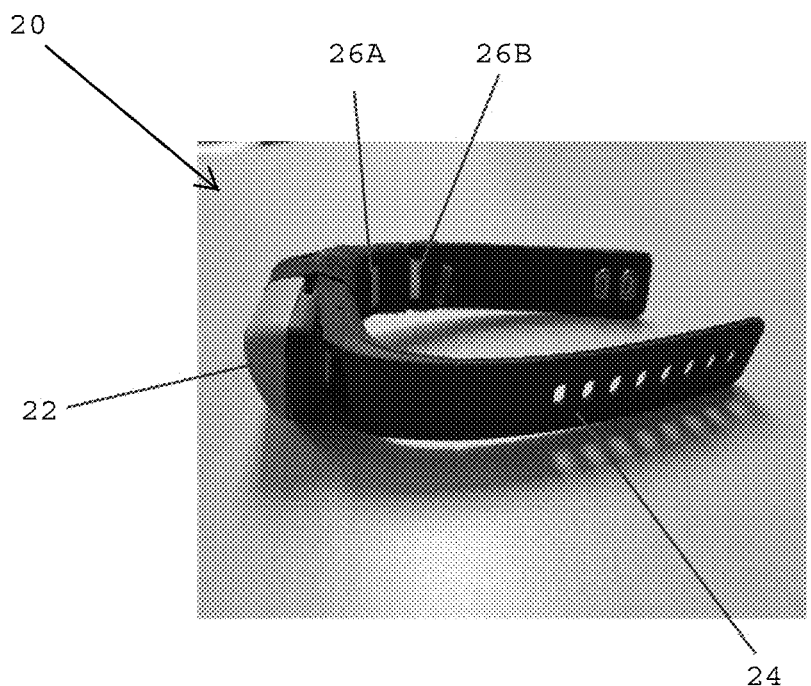
FIG. 1 shows a perspective view of a wearable fatigue alert device, in accordance with one embodiment of the present patent application.

Referring to FIG. 1, in one embodiment, a wearable fatigue alert device 20 preferably includes a housing 22 that is secured to a wristband 24. In one embodiment, the wristband 24 may be made of silicone and/or polymer materials. The wearable fatigue alert device 20 desirably includes sensors 26A, 26B that are located on the wristband 24. When the device 20 is worn over a wrist, the sensors 26A, 26B are preferably configured for obtaining biofeedback data from a wearer for determining the fatigue status of an individual.

Figure 2:
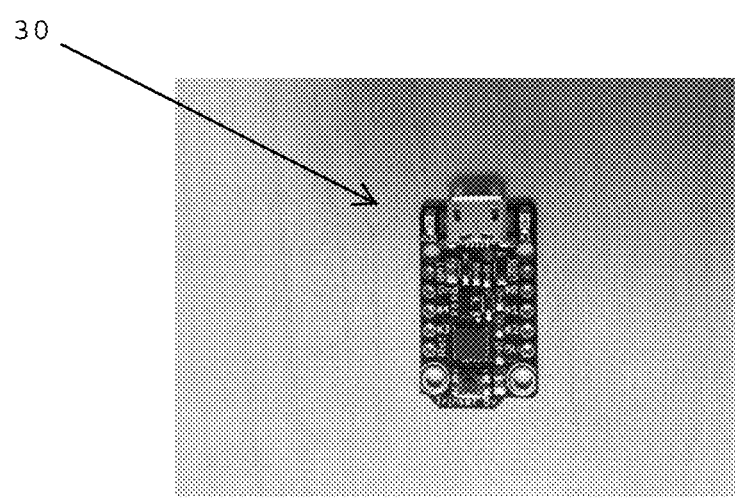
FIG. 2 shows a circuit board for a wearable fatigue alert device, in accordance with one embodiment of the present patent application.

Referring to FIG. 2, in one embodiment, the wearable fatigue alert device 20 preferably includes a circuit board 28 having a microprocessor 30 that is in communication with the sensors 26A, 26B. The sensors 26A, 26B preferably collect and communicate the biofeedback data of a wearer to the microprocessor 30, which generates an alert (e.g., vibration, sound, light) that notifies a wearer that they are becoming fatigued. In one embodiment, the microprocessor 30 desirably incorporates Electrodermal Activity (EDA) technology for evaluating the fatigue status of a wearer.

Figure 3:
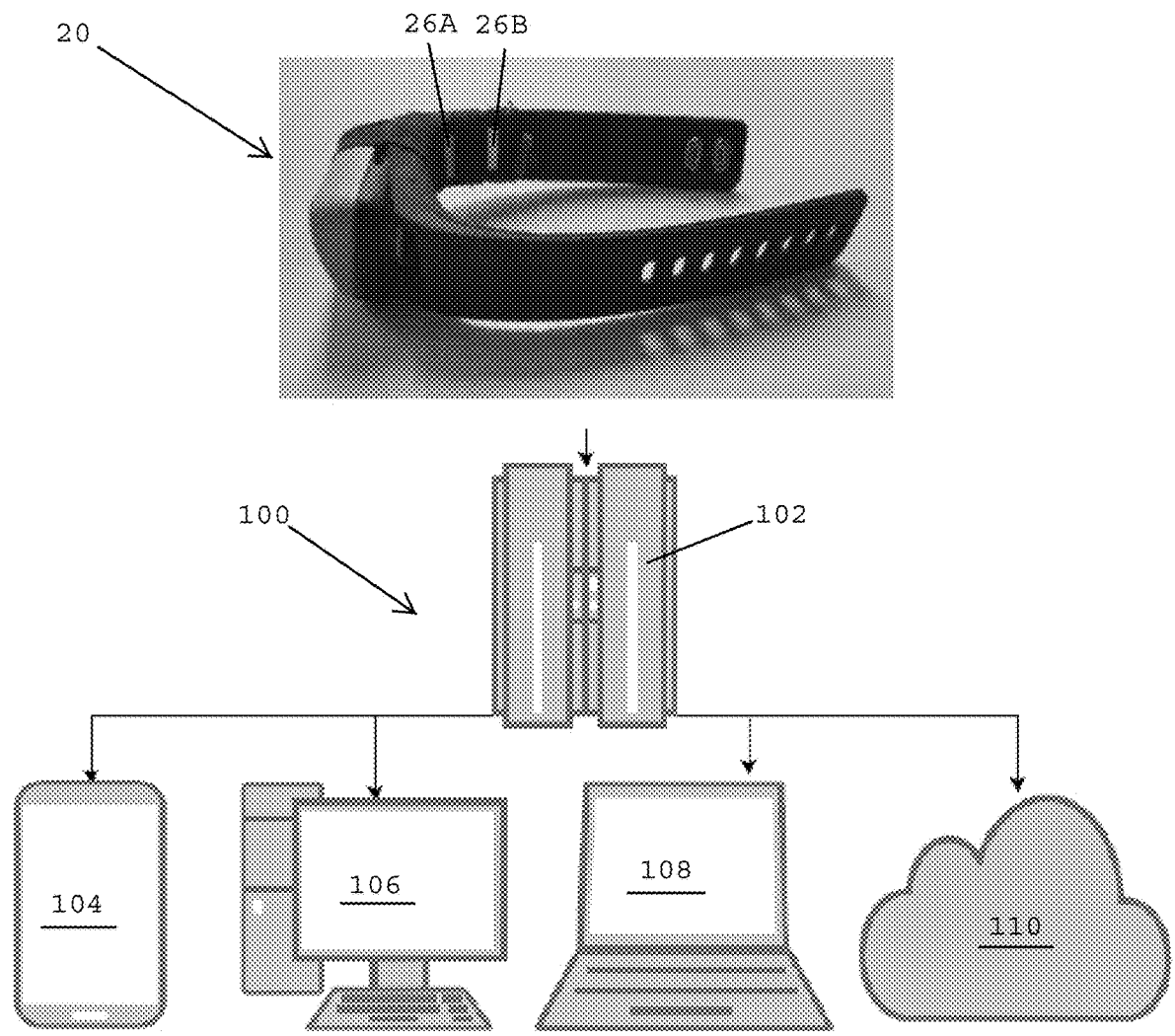
FIG. 3 shows a schematic view of a wireless, web-based system for operating a wearable fatigue alert device, in accordance with one embodiment of the present patent application.

Referring to FIG. 3, in one embodiment, one or more wearable fatigue alert devices 20 may be linked with a wireless, web-based system 100 that preferably includes one or more servers 102 that contain information databases and computer programs (e.g., software programs; software applications; Apps). In one embodiment, the one or more wearable fatigue alert devices 20 may be in wireless communication with the system 100 so that each of the wearable devices may send information to the one or more servers 102 and receive information and updates from the one or more servers 102.

In one embodiment, an operator or user may sign-on, activate, connect and/or enroll one or more of the wearable fatigue alert devices 20 into a fatigue status monitoring program that is operated, maintained, and controlled by the system 100. In one embodiment, the system 100 preferably enables operators to use portable devices such as smart phones and tablets 104, desk top computers 106, lap top computers 108, and/or a Cloud computing network 110 to sign-in, activate enroll, update, and/or monitor the operation and performance of the one or more wearable fatigue alert devices that are linked with the system.

In one embodiment, a new user of a wearable fatigue alert device 20 may activate and/or enroll his or her wearable device into the system 100 to enter the program and establish a baseline for using the device. In one embodiment, after initially linking the wearable device 20 with the system 100, a new user will wear the device 20 for a period of time (e.g., an entire day; at least 24 hours) so that the sensors 26A, 26B are able to obtain and record data about the user during the period of time. This initial time period for establishing a base line for a user may be termed a "test flight" period during which the wearable device 20 may be closely tracked, monitored and calibrated. During the startup time period for establishing the baseline, the user will preferably go through his or her normal activities, such as waking up, bathing, eating, exercising, sleeping, napping, commuting, working, playing, relaxing, etc. Before, during, and/or after data has been recorded by the sensors 26A, 26B and recorded by the system 100, the user or a third party may be asked a series of questions in order to associate a user's activities with certain times and readings obtained by the sensors 26A, 26B. Thus, the system 100 will preferably build a user profile for each individual wearing one of the wearable fatigue alert devices, which will enable the system to accurately determine when the individual users are alert and when the individual users are fatigued.

As used herein, "Cloud computing" means the on-demand availability of computer system resources, especially data storage and computing power, without direct active management by the user. The term is generally used to describe data centers available to many users over the Internet. Large cloud computing networks often have functions distributed over multiple locations from central servers. See https://en.wikipedia.org/wiki/Cloud_computing.

In one embodiment, the system may use artificial intelligence (AI) when monitoring the activities of users and establishing baselines for the users to determine when the users are alert and when the users are fatigued.

In one embodiment, the system may be used to monitor the activities of a large group of vehicle operators (e.g., truck drivers), each of whom is wearing one of the wearable fatigue alert devices 20. For example, a trucking company may operate the system 100 via a central hub for tracking the alert and fatigue status of each of its drivers wearing a device 20 for improving trucking operations and safety. In another embodiment, a train system may have each of its engineers and conductors wear one of the wearable fatigue alert devices 20 for tracking the alert and fatigue status of its train operators. In one embodiment, a system linked with a train may remotely and/or automatically slow down the speed of the train and/or completely stop the train on the tracks if it receives feedback information that an engineer or conductor is fatigued or drowsy. The system disclosed herein may be used to track and monitor the alert and fatigue status of all types of individuals who operate vehicles, such as cars, vans, taxis, buses, trucks, trains, subways, airplanes, helicopters, etc. In one embodiment, the systems disclosed herein may be used to monitor the fatigue status of soldiers and/or military personnel to provide commanders with real time information from the battlefield.

Figure 4:
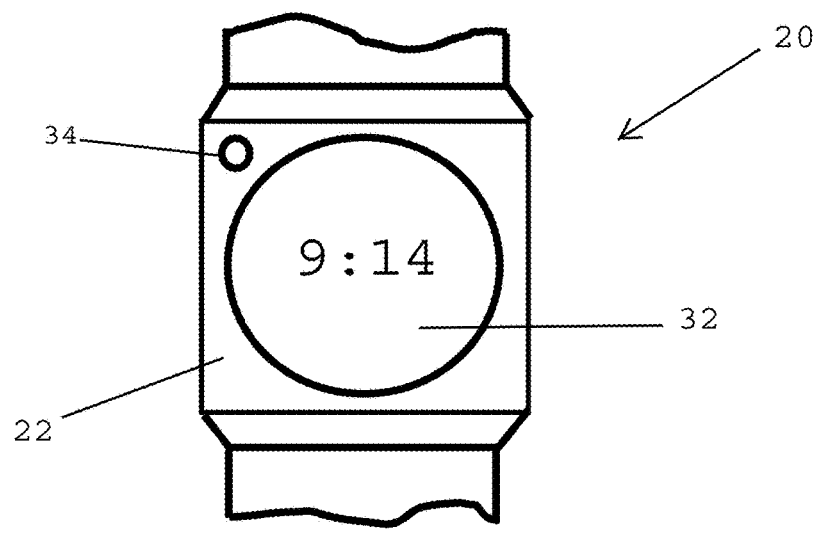
FIG. 4 shows a front face of a wearable fatigue alert device including a display screen for displaying information to a wearer, in accordance with one embodiment of the present patent application.

Referring to FIG. 4, in one embodiment, the wearable fatigue alert device 20 may include many features that are present in a smart watch and/or a smart phone. In one embodiment, the wearable fatigue alert device 20 preferably includes a visual display screen 32 that may display video images and pictures. In one embodiment, the visual display screen 32 may display time so that in addition to being used as a fatigue alert device, the device 20 may also be used as a watch for determining time.

In one embodiment, the wearable fatigue alert device 20 may include an optical sensor 34 that tracks eye movement of an individual wearing the device for obtaining information that may be used for determining the fatigue status of the individual. In one embodiment, the optical sensor 34 may be located on the housing 22 of the device 20. In one embodiment, the optical sensor 34 may use light within the infrared range.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A wearable fatigue alert device comprising:
a housing;
a wristband, wherein said housing is secured to said wristband;
at least one sensor located on said wristband, wherein said at least one sensor is configured to obtain biofeedback data from a wearer for determining a fatigue status of an individual; and
an optical sensor that tracks eye movement for gathering information about the fatigue status of an individual.

2. The device as claimed in claim 1, further comprising a circuit board disposed within said housing, wherein said circuit board includes at least one microprocessor that is in communication with said at least one sensor located on said wristband, and wherein said at least one sensor is configured to collect and communicate the biofeedback data to said at least one microprocessor.

3. The device as claimed in claim 2, wherein said at least one microprocessor comprises code for generating an alert signal for notifying the wearer that they are becoming fatigued.

4. The device as claimed in claim 3, wherein said alert signal is selected from the group consisting of vibration signals, audible signals, and light signals.

5. The device as claimed in claim 2, wherein said microprocessor includes code that utilizes Electrodermal Activity (EDA) technology for evaluating the fatigue status of the wearer.

6. The device as claimed in claim 1, wherein said housing comprises a visual display screen for displaying information.

7. The device as claimed in claim 6, wherein the information that is displayed on said visual display screen includes time.

8. The device as claimed in claim 1, wherein said optical sensor operates within the infrared spectrum of light.

9. A system for monitoring fatigue status of vehicle operators comprising:
one or more central processing units containing one or more databases and one or more software programs adapted to monitor the fatigue status of the vehicle operators;
a plurality of wearable fatigue alert devices in wireless communication with said one or more central processing units;
each said wearable fatigue alert device comprising
a housing,
a wristband, wherein said housing is secured to said wristband, and
at least one sensor located on said wristband, wherein said at least one sensor is configured to obtain biofeedback data from the vehicle operators for determining the fatigue status of the vehicle operators; and
an optical sensor that tracks eye movement for gathering information about the fatigue status of the vehicle operators.

10. The system as claimed in claim 9, wherein said one or more software programs include a wireless, web-based protocol for enabling said wearable fatigue alert devices to be linked with portable devices, smart phones, tablets, desk top computers, lap top computers, and Cloud computing networks.

11. The system as claimed in claim 9, wherein said one or more software programs includes an initial set-up protocol that enables the vehicle operators to wear one of said wearable fatigue alert devices for a period of time to establish a baseline for determining when is the vehicle operators are alert and when is the one or more vehicle operators are fatigued.

12. The system as claimed in claim 9, wherein said one or more central processing units include artificial intelligence (AI) for collecting information about the vehicle operators and developing user profiles for each of the vehicle operators.

13. The system as claimed in claim 9, wherein each said wearable fatigue alert device comprises a circuit board disposed within said housing, wherein said circuit board includes at least one microprocessor that is in communication with said at least one sensor located on said wristband, and wherein said at least one sensor is configured to collect and communicate the biofeedback data to said at least one microprocessor.

14. The system as claimed in claim 13, wherein said at least one microprocessor comprises code for generating an alert signal for notifying the vehicle operators that they are becoming fatigued.

15. The system as claimed in claim 14, wherein said alert signal is selected from the group consisting of vibration signals, audible signals, and light signals.

16. The system as claimed in claim 9, wherein said one or more software programs include code that utilizes Electrodermal Activity (EDA) technology for evaluating the fatigue status of the vehicle operators.

17. The system as claimed in claim 9, wherein said housing of said wearable fatigue alert device comprises a visual display screen for displaying information.

18. The system as claimed in claim 17, wherein the information that is displayed on said visual display screen includes time.

19. The system as claimed in claim 9, wherein said optical sensor that tracks eye movement operates within the infrared spectrum of light.

20. The system as claimed in claim 9, wherein said system is linked to a vehicle to remotely slow down or completely stop the vehicle upon receiving feedback information from said wearable fatigue alert device that one of the vehicle operators associated with the vehicle is fatigued or drowsy.

* * * * *